United States Patent [19]

Maeda et al.

[11] Patent Number: 5,417,061
[45] Date of Patent: May 23, 1995

[54] DEVICE FOR DETECTING CATALYST DETERIORATION FOR AN INTERNAL COMBUSTION ENGINE

[75] Inventors: Mie Maeda; Hirofumi Ohuchi, both of Himeji, Japan

[73] Assignee: Mitsubishi Denki Kabushiki Kaisha, Tokyo, Japan

[21] Appl. No.: 272,649

[22] Filed: Jul. 11, 1994

Related U.S. Application Data

[63] Continuation of Ser. No. 946,532, Sep. 17, 1992, abandoned.

[30] Foreign Application Priority Data

Oct. 14, 1991 [JP] Japan ................. 3-264312

[51] Int. Cl.⁶ ................................. F01N 3/00
[52] U.S. Cl. ................................. 60/277
[58] Field of Search ............... 60/276, 277; 123/691

[56] References Cited

U.S. PATENT DOCUMENTS 3,939,654  2/1976  Creps ..................... 60/276
5,157,919  10/1992  Gopp ..................... 60/274

FOREIGN PATENT DOCUMENTS 3443649  6/1986  Germany .
3916467  11/1990  Germany .
197737  9/1986  Japan .

OTHER PUBLICATIONS

"Detections of Catalyst Performance Loss Using On-Board Diagnostics" SAE 900062, Clemmens et al–Feb. 1990.

*Primary Examiner*—Noah P. Kamen
*Attorney, Agent, or Firm*—Sughrue, Mion, Zinn, Macpeak and Seas

[57] ABSTRACT

A device for detecting the deterioration of a catalyst wherein oxygen sensors are provided on the upstream and downstream sides of the catalytic converter. Circuitry is provided for calculating integration values corresponding to areas surrounded by output signals of the oxygen sensors and designated signals; for calculating time periods between which the sensor signals reverse polarity with respect to the designated signals; for calculating a parameter for determining deterioration of the catalyst based on the integration values, the time periods or a combination of both; for determining deterioration of the catalyst by comparing the calculated parameter with a predetermined value; and for issuing an alarm when the catalyst is determined as deteriorated.

3 Claims, 6 Drawing Sheets

DEVICE FOR DETECTING CATALYST DETERIORATION FOR AN INTERNAL COMBUSTION ENGINE

This is a Continuation of Application Ser. No. 07/946,532 filed Sep. 17, 1992, now abandoned.

BACKGROUND OF THE INVENTION

1. Field of the Invention

This invention relates to a device for detecting the deterioration of a catalyst in an internal combustion engine wherein air-fuel ratio sensors (oxygen sensors) are provided on the upstream side and the downstream side of a catalytic converter installed for purifying the exhaust gas in an internal combustion engine, and for alarming a driver.

2. Discussion of Background

Conventionally, in the fuel injection control of an internal combustion engine, a basic injection quantity of a fuel injection valve is calculated in accordance with an intake quantity and a revolution at speed of the engine. The basic injection quantity is corrected in accordance with an air-fuel ratio correction calculated based on a detected signal of an oxygen sensor for detecting an oxygen concentration in the exhaust gas. An actually supplied fuel quantity is controlled in accordance with the corrected injection quantity. This control is repeatedly performed, which finally converges the air-fuel ratio of the engine in a predetermined range.

In the fuel injection control, the air-fuel ratio is controlled within a very narrow range adjacent to a theoretical air-fuel ratio by a feedback control with respect to the air-fuel ratio. Furthermore, the purification capability of a three-way catalytic converter provided at the exhaust system, that is, a capability for converting poisonous components in the exhaust gas; CO, $NO_x$ and HC to harmless ones by oxidation and reduction reactions, can be highly maintained.

In the above air-fuel ratio control, the heating or poisoning of the exhaust gas lowers a response speed of the oxygen sensor, lowers an output voltage thereof, and elevates an activation temperature thereof. With respect to the catalyst, the lowering of its purification efficiency and elevation of its activation temperature thereof are caused. A measure against the lowering of the performances, is described, for instance, in Japanese Unexamined Patent Publication 197737/1986, as follows.

(a) Oxygen sensors are provided respectively upstream and downstream from a catalyst and an activation determining means is provided. The air-fuel control is performed by using the two oxygen sensors or either activated one of the oxygen sensors.

(b) With deterioration of a response characteristic of an oxygen sensor, a control period of a feedback control of the air-fuel ratio is accelerated, thereby preventing deterioration in a response characteristic of the total system.

However, the conventional device responds to deterioration of the oxygen sensor, and not to deterioration or destruction of the catalyst per se. Accordingly, since a driver can not detect a failure, he runs a vehicle emitting poisonous substances.

SUMMARY OF THE INVENTION

It is an object of the present invention to provide a device for detecting the deterioration of a catalyst in an internal combustion engine, capable of determining the deterioration or destruction of a catalyst by always monitoring a catalyst state and informing a driver of a failure.

According to a first aspect of the present invention, there is provided a device for detecting the deterioration of a catalyst in an internal combustion engine adapted to a system wherein a catalytic converter is provided for purifying exhaust gas in an exhaust system of the internal combustion engine, oxygen sensors are provided on the upstream side and the downstream side of the catalytic converter and an air-fuel control is performed in accordance with outputs of the oxygen sensors, comprising:

means for calculating integration values corresponding to areas of figures surrounded by output signals of the oxygen sensors and designated or predetermined signals;

means for calculating periods wherein the output signals reverse with respect to the designated signals;

means for calculating a parameter for determining the deterioration of the catalyst based on said values corresponding to the areas or said periods, or a combination of the values corresponding to the areas and the periods;

deterioration determining the means for determining deterioration of the catalyst by comparing said parameter with a predetermined value; and alarm means for issuing an alarm when the catalyst is determined as deteriorated.

According to a further aspect of the present invention, the designated values are corrected by a hysteresis factor.

According to another aspect of the present invention, the parameter for determining deterioration is calculated by mean values or summation values of the values corresponding to the areas or the periods in a predetermined time.

In the first aspect of the present invention, the areas surrounded by the output signals of the oxygen sensors provided upstream and downstream from the catalytic converter and the designated signals, and the period wherein the output signals reverse with respect to the designated signals, are calculated. The parameter for determining deterioration of the catalyst is calculated from the areas, the reversing periods, or a combination of both. By comparing the parameter for determining deterioration with the predetermined value, the deterioration is determined. When the deterioration is determined, an alarm is issued.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

EXAMPLE 1

Figure 1:
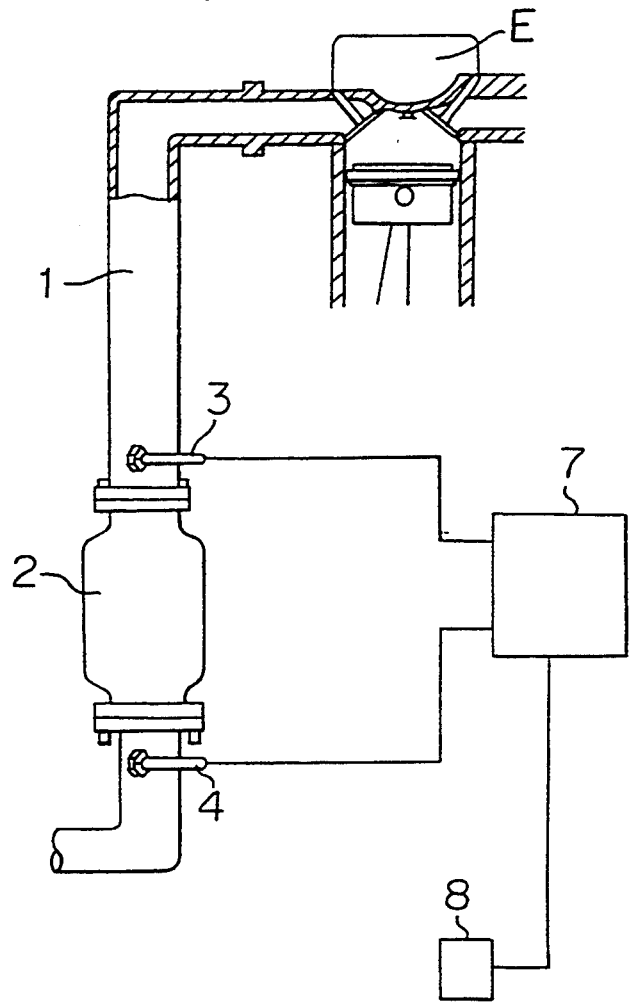
FIG. 1 is a construction diagram of the invented

Referring to the drawings, in FIG. 1 reference numeral 1 designates an exhaust pipe of an engine E, 2, a catalytic converter for purifying the exhaust gas, connected to the middle of the exhaust pipe 1, 3 and 4, first and second oxygen sensors (air-fuel ratio sensors) provided on the upstream side and the downstream side of the catalytic converter 2, 7, means for detecting deterioration of the catalyst from the outputs of the first and second oxygen sensors 3 and 4, and 8, an alarm means for outputting an alarm to a driver when the detecting means detects deterioration of the catalyst.

In the above construction, the oxygen sensors 3 and 4 detect the oxygen concentration in the exhaust gas, and the respective outputs thereof are outputted to the detecting means for catalyst deterioration. Upon receiving the outputs, the detecting means 7 detects whether the catalyst is deteriorated or not. When the catalyst is determined as deteriorated, the detecting means outputs the determination result to the alarm means 8 to issue an alarm.

Figure 2:
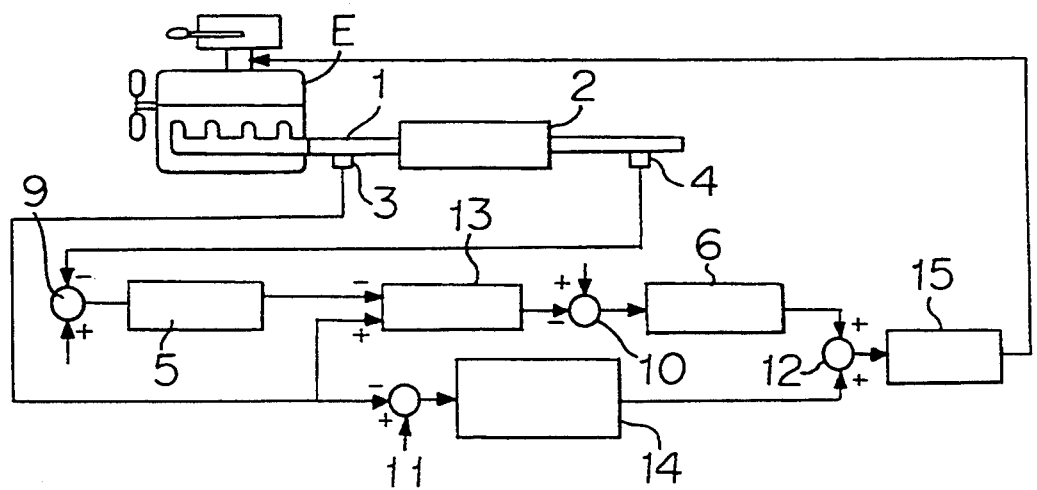
FIG. 2 is a construction diagram of an air-fuel ratio control system according to the present invention.

FIG. 2 shows an air-fuel ratio control system utilizing the two oxygen sensors 3 and 4. Reference numerals 5 and 6 designate integrators, 9 through 12, adders, 13, a comparator, 14, a proportional control unit, and 15, an amplifier. In this control system, a feed back control of the air-fuel ratio is performed by correcting a criteria level depending on whether the air-fuel ratio is "rich" or "lean" based on the output of the oxygen sensor 3 on the upstream side of the catalytic converter 2, as modified via the adder 9 and the integrator 5 in accordance with the output of the oxygen sensor 4 on the downstream side thereof.

Figure 3A:
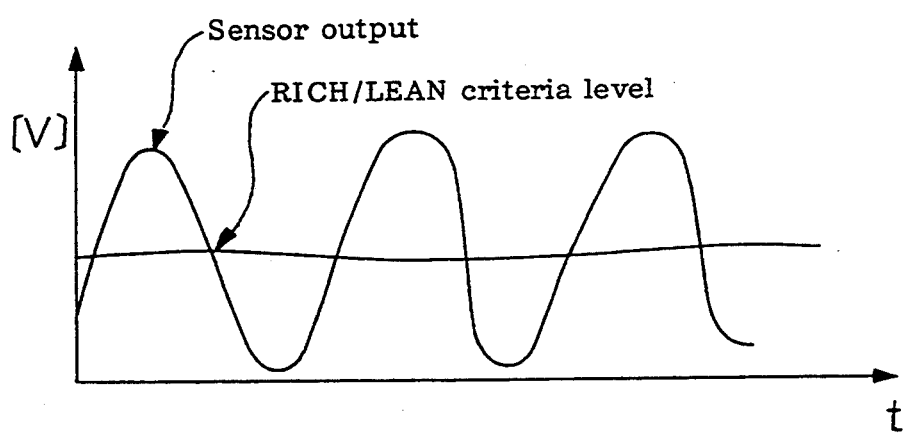
FIGS. 3 (a) and 3 (b) are characteristic diagrams of the respective oxygen sensors when a catalyst is normal, according to the present invention.
Figure 3B:
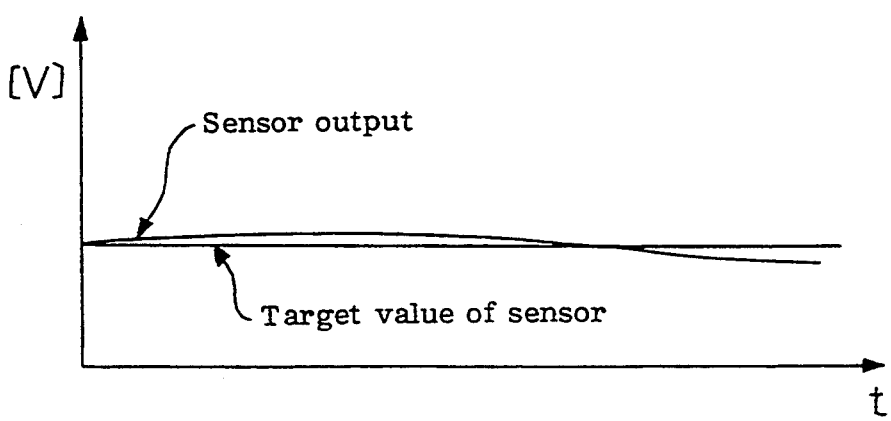
Figure 4A:
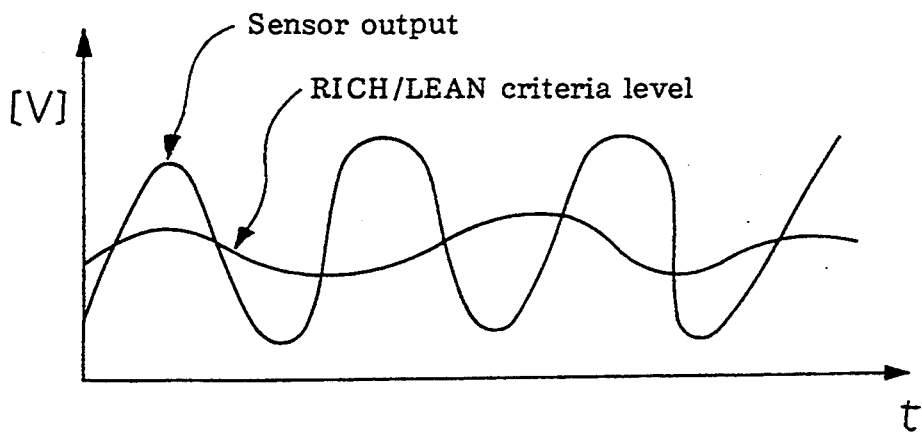
FIGS. 4(a) and 4(b) are characteristic diagrams of the respective oxygen sensors when the catalyst is deteriorated, according to the present invention.
Figure 4B:
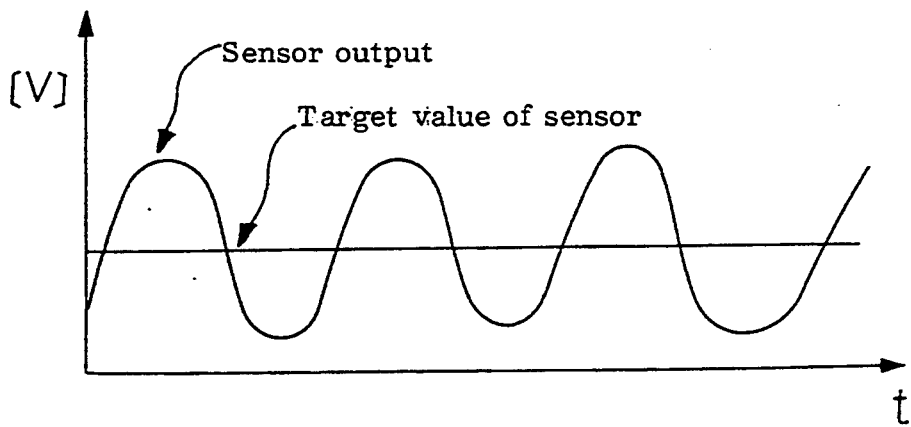

FIGS. 3(a) and 3(b) show characteristics of the oxygen sensors when the catalyst is normal. FIG. 3(a) shows an output of the upstream side oxygen sensor 3 and a RICH/LEAN criteria level, whereas FIG. 3(b) shows an output of the downstream side oxygen sensor 4 and its target value. FIGS. 4(a) and 4(b) show characteristics of the oxygen sensors when the catalyst is deteriorated. FIG. 4(a) shows an output of the upstream side oxygen sensor 3 and a monitoring RICH/LEAN criteria level, whereas FIG. 4(b) shows an output of the downstream side oxygen sensor 4 and its target value. As is apparent from these Figures, the deterioration of the catalyst is detected from an output variation of the downstream side oxygen sensor 4.

Figure 5:
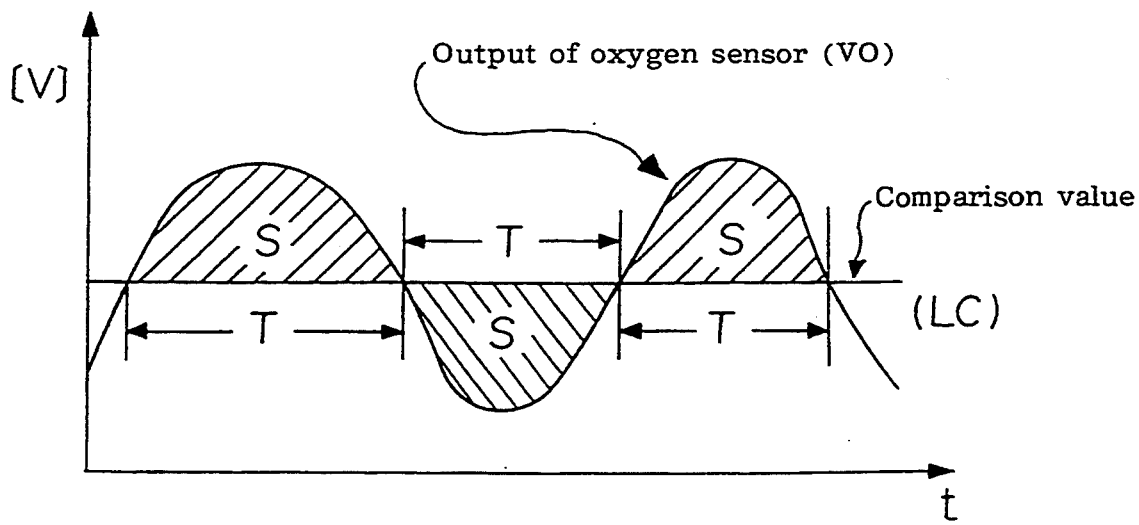
FIG. 5 is an explanatory diagram for detecting deterioration of the catalyst by the invented device.

Next, the detection of deterioration of the catalyst is to be explained by FIG. 5. VO designates the output signals of the oxygen sensors 3 and 4, and LC, a comparison value, that is, the RICH/LEAN criteria level or the target value. S designates an area (an integration value corresponding to area) surrounded or enclosed by VO and LC, and T, an output reversing period of VO with respect to LC. The deterioration of the catalyst is determined by S or T or a combination of S and T.

Figure 6:
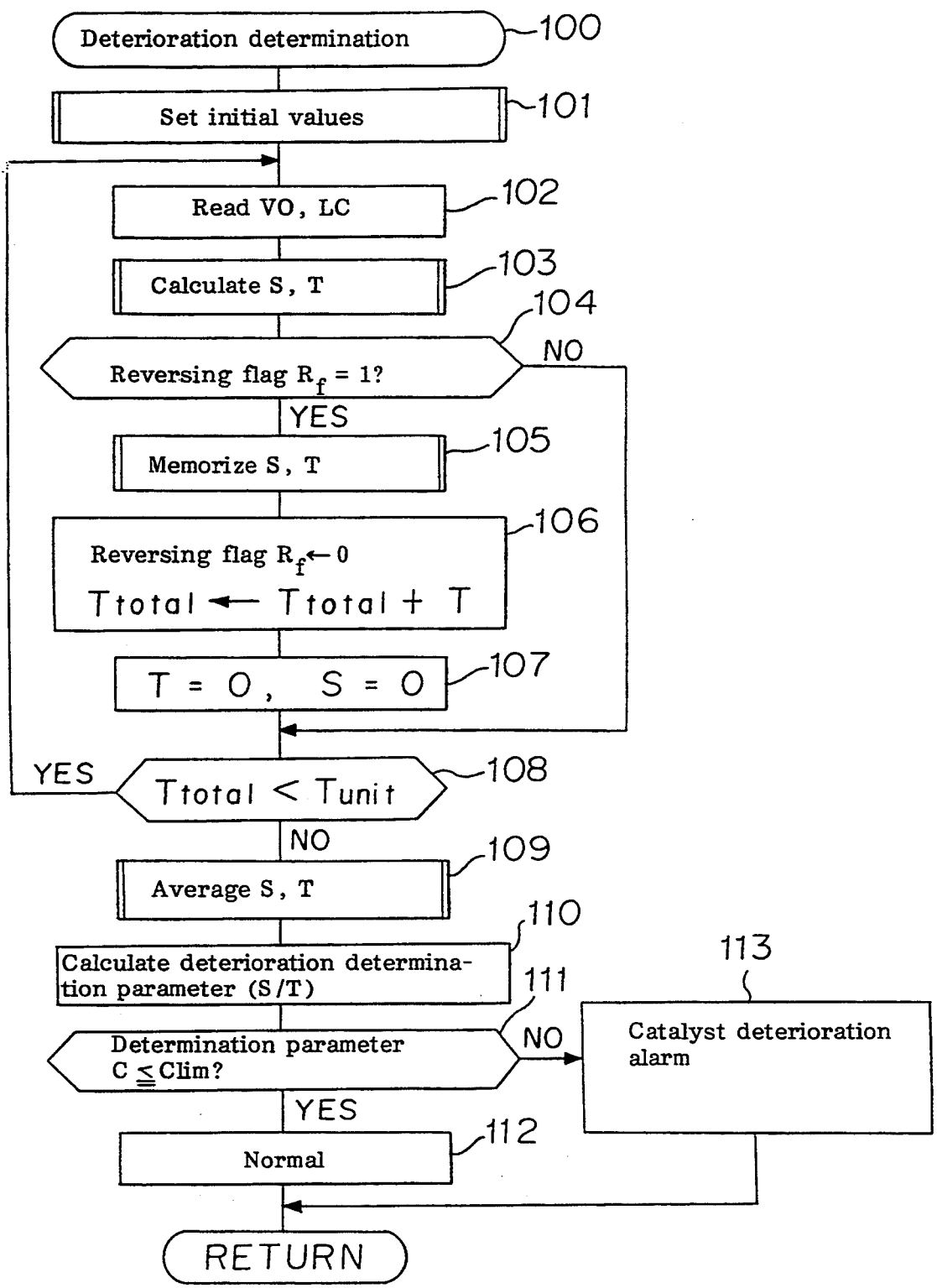
FIG. 6 is a flowchart showing the operation of the invented device.

Next, an explanation will be given of the operation of the detecting means for catalyst deterioration 7 shown in FIG. 1 according to a flowchart of FIG. 6. First, in step 101, the operation initializes respective values as shown in FIG. 8. In step 102, the operation reads the output signals VO of the oxygen sensors 3 and 4 and the comparison value LC. In step 103, the operation calculates the areas S and the reversing periods T, which is to be explained by the flowchart of FIG. 7.

Figure 7:
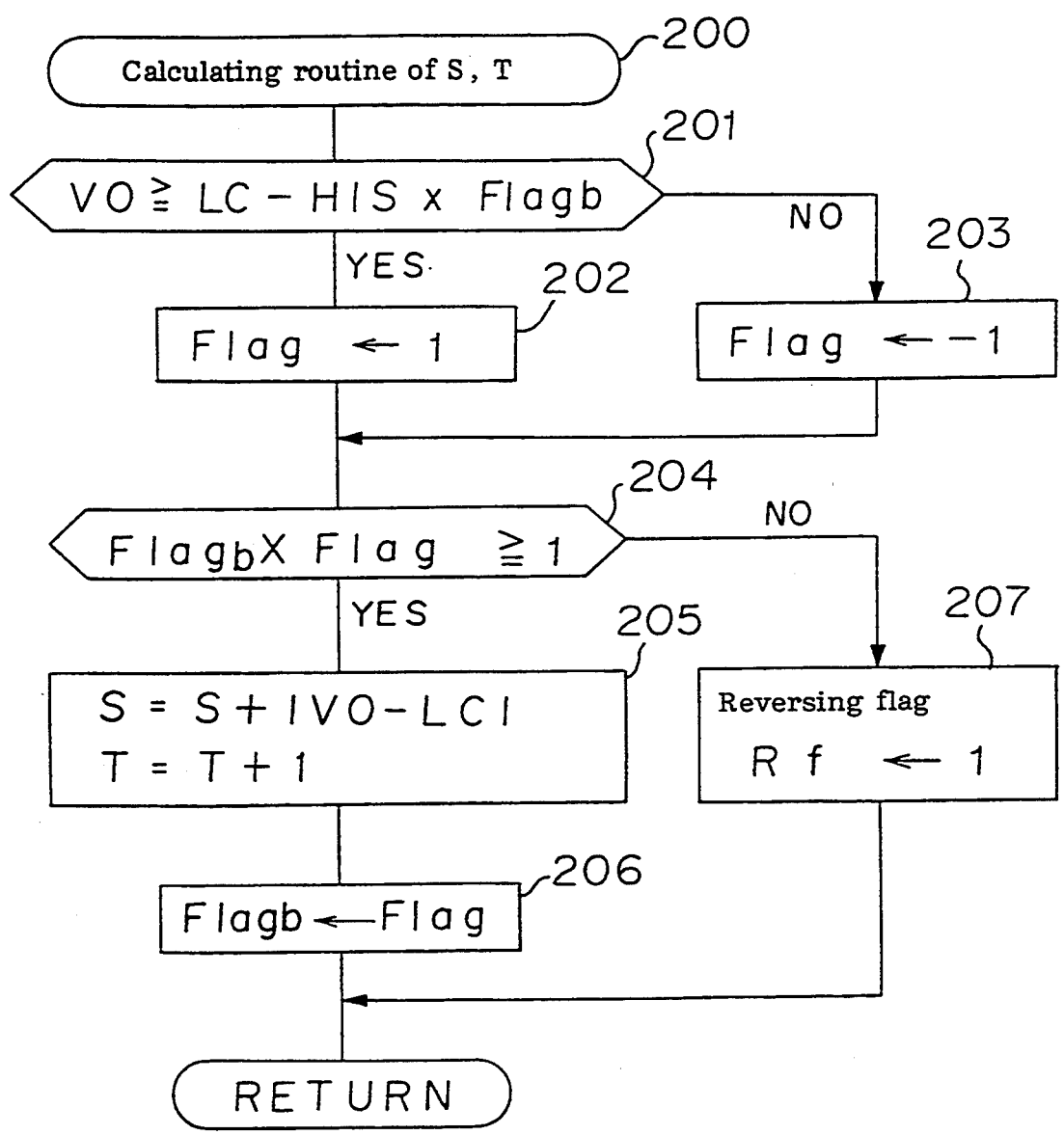
FIG. 7 is a flowchart showing the operation of calculating S and T of the invented device.
Figure 8:
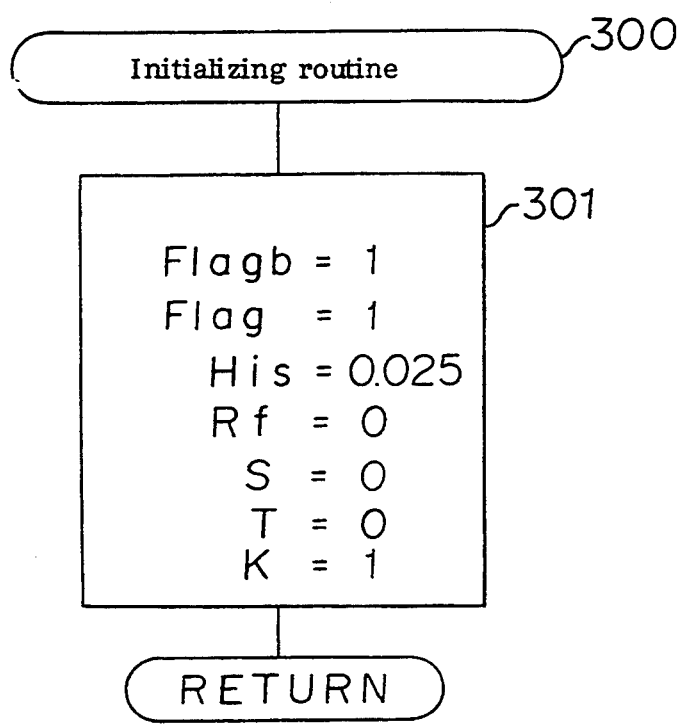
FIG. 8 is a flowchart showing an initializing operation of the invented device.

In the calculating routine for S and T shown in FIG. 7, in step 201, the operation compares VO and LC (which is actually reduced by a hysteresis error His×Flag b). When VO≧LC, the operation proceeds to step 202, and sets a comparison determining flag as Flag=1. When VO<LC, the operation proceeds to step 203, and sets the flag as Flag=−1. In step 204, the operation determines whether a preceding comparison determining Flag b differs from a current comparison determination Flag, that is, whether the or relationship between VO and LC is reversed. When it is reversed, in step 207, the operation sets a reversing flag Rf as Rf=1, and the routine is finished. When Flag b=Flag, that is, when it is not reversed, the operation proceeds to step 205, and determines S and T as S=S+|VO−LC| and T=T+1, respectively. In step 206, the operation replaces Flag b with Flag and the routine is finished.

Figure 9:
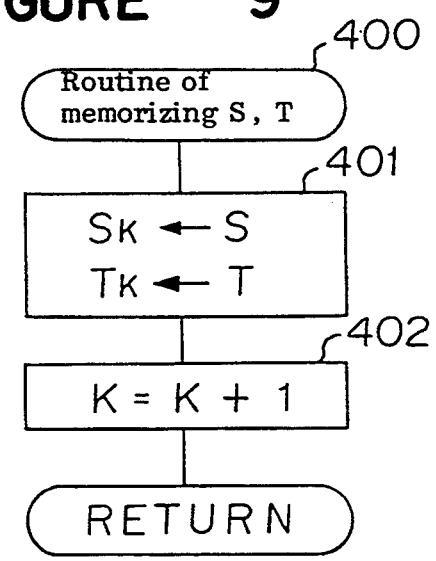
FIG. 9 is a flowchart showing the operation of memorizing S and T of the invented device.

Next, in step 104 the operation determines whether Rf=1. When Rf=0, the operation proceeds to step 108. When Rf=1, the operation proceeds to step 105 and memorizes the calculated S and T as shown in FIG. 9. In step 106, the operation determines Rf as Rf=0 and an elapsed time $T_{total}$ as $T_{total}=T_{total}+T$. In step 107, the operation determines T and S as T=0 and S=0, respectively. In step 108, the operation repeats the treatment of steps 102 through 107 until the elapsed time $T_{total}$ equals or exceeds a predetermined time $T_{unit}$ (for instance, 20 second).

Figure 10:
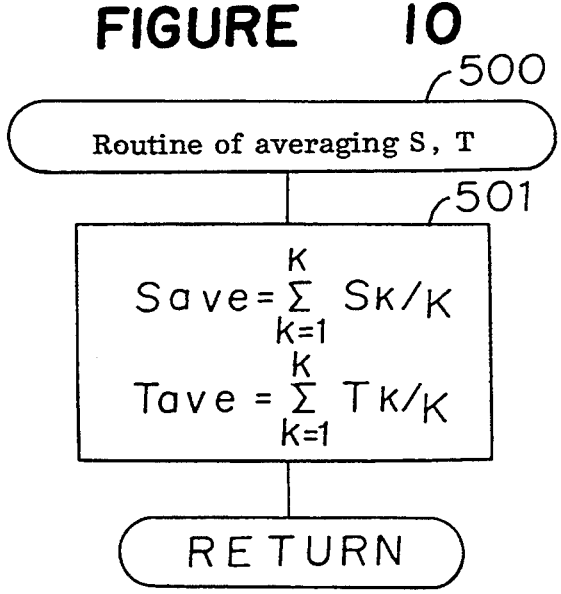
FIG. 10 is a flowchart showing the operation of averaging S and T of this invented device.

When the elapsed time $T_{total}$ reaches the predetermined time $T_{unit}$ in step 108, the operation performs an average treatment of the series $S_n$ ($S_1$, $S_2$, ...) and $T_n$ ($T_1$, $T_2$, ...) which are calculated and memorized within the predetermined time $T_{unit}$ as shown in FIG. 10, in step 109. The operation calculates average values of S and T or $S_{ave}$ and $T_{ave}$ as follows:

$$S_{ave}=(S_1+S_2+\ldots+S_k)/K$$

$$T_{ave}=(T_1+T_2+\ldots+T_k)/K$$

The values of $S_{ave}$ and $T_{ave}$ are obtained respectively for the oxygen sensors 3 and 4.

In step 110, the operation calculates a parameter for determining deterioration C by using $S_{ave}$ and $T_{ave}$, for instance, as $C=S_{ave}/T_{ave}$ by using $S_{ave}$ and $T_{ave}$ of the oxygen sensor 4. In step 111, the operation compares the parameter C with a predetermined value $C_{lim}$. When the parameter C is equal to or less than the predetermined value $C_{lim}$, in step 112, the operation determines that the catalyst is normal and the deterioration determination routine is finished. When the parameter C is larger than the predetermined value $C_{lim}$, the operation proceeds to step 113 which determines that the catalyst is deteriorated, and transmits the determination signal to the alarm means 8 to issue an alarm.

EXAMPLE 2

In Example 2, with respect to S and T obtained in Example 1, the operation obtains the area S(plus) and the reversing period T (plus) when VO≧LC, and the area S (minus) and the reversing period T (minus) when VO<LC. The operation utilizes S and T to determine deterioration, which are calculated by the following equations; S=S (plus)+S (minus) and T=T (plus)+T (minus).

EXAMPLE 3

In Example 3, the operation utilizes the area $S_{front}$ obtained from the output of the upstream oxygen sensor 3 and the area $S_{rear}$ obtained by the output of the downstream oxygen sensor 4, and calculates the parameter for determining deterioration C by the following equation $C = S_{rear}/S_{front}$.

EXAMPLE 4

In Example 1, an averaging treatment of S and T is performed. Instead, in Example 4, the operation obtains summation values $S_{sum}$ of $S_s$ of the respective oxygen sensors 3 and 4 as $S_{sum} = S_1 S_2 + \ldots + S_k$, and obtains the parameter for determining deterioration C as C=(upstream side $S_{sum}$)/(downstream side $S_{sum}$).

EXAMPLE 5

In Example 1, the operation obtains the areas S and the reversing periods T for the respective oxygen sensors 3 and 4. In Example 5, the operation performs the deterioration determination based on S and T of the upstream side oxygen sensor 3 and S and T by the downstream side oxygen sensor 4 by the following equation:

C=(upstream side S/upstream side T)/(downstream side S/downstream side T)

EXAMPLE 6

In Example 6, the operation utilizes the reversing periods $T_{front}$ obtained from the output of the upstream side oxygen sensor 3 and the reversing period $T_{rear}$ obtained from the output of the downstream side oxygen sensor 4, and performs the deterioration determination on the basis of $C = T_{front}/T_{rear}$.

As stated above, according to the present invention, the two oxygen sensors are provided on the upstream and downstream sides of the catalytic converter. The areas encompassed between the output signals of the oxygen sensors and a predetermined signal, and the time periods at which the sensor signals reverse or cross the predetermined signal, are calculated. A parameter for determining deterioration is calculated from the integrated areas and the reversing periods, based on which the deterioration of the catalyst is determined. Accordingly, the lowering of performance of the catalytic converter can be detected at an early stage and the emission of poisonous exhaust gas components is minimized.

Furthermore, since the predetermined signal is corrected by a hysteresis factor, the determination of the deterioration can accurately be performed.

Furthermore, the parameter for determining deterioration is calculated based on the average value or the summation (integrated) value of the areas and the reversing periods in a certain period of time, by which the determination of deterioration can more accurately be performed.

Obviously, numerous modifications and variations of the present invention are possible in light of the above teachings. It is therefore to be understood that within the scope of the appended claims, the invention may be practiced otherwise than as specifically described herein.

What is claimed is:

1. A device for detecting the deterioration of a catalyst for an internal combustion engine, wherein a catalytic converter is provided for purifying exhaust gas in an exhaust system of the internal combustion engine, oxygen sensors are provided on an upstream side and a downstream side of the catalytic converter, and an air-fuel ratio control is performed in accordance with outputs of the oxygen sensors, said device comprising:

a) means for calculating individual integration values (S) corresponding to areas enclosed by output signals of the oxygen sensors and designated signals, wherein a designated signal for the upstream sensor is variable in accordance with the output signal of the downstream sensor, and the integration values are calculated for areas both above and below an associated designated signal;

b) means for determining variable, individual time periods (T) between which the output signals reverse polarity with respect to the designated signals;

c) means for calculating a parameter (C) for determining deterioration of the catalyst based on a selected one of said integration values, said time periods, and a combination of the integration values and the polarity reversal time periods;

d) deterioration determining means for determining deterioration of the catalyst by comparing said parameter with a predetermined value ($C_{lim}$); and e) alarm means for issuing an alarm when the catalyst is determined as deteriorated.

2. The detecting device according to claim 1, wherein the designated signals are corrected by a hysteresis factor.

3. The detecting device of deterioration of a catalyst for an internal combustion engine according to claim 1 or claim 2, wherein the parameter for determining deterioration is calculated from one of mean values and summation values of one of the integration values and the polarity reversal time periods in a predetermined time.

* * * * *